United States Patent
Lewellen et al.

(10) Patent No.: US 9,330,879 B2
(45) Date of Patent: May 3, 2016

(54) BREMSTRAHLUNG TARGET FOR INTENSITY MODULATED X-RAY RADIATION THERAPY AND STEREOTACTIC X-RAY THERAPY

(76) Inventors: John Lewellen, Seaside, CA (US); John Noonan, Naperville, IL (US)

( * ) Notice: Subject to any disclaimer, the term of this patent is extended or adjusted under 35 U.S.C. 154(b) by 139 days.

(21) Appl. No.: 14/131,317

(22) PCT Filed: Aug. 6, 2012

(86) PCT No.: PCT/US2012/049731
§ 371 (c)(1),
(2), (4) Date: Mar. 13, 2014

(87) PCT Pub. No.: WO2013/020130
PCT Pub. Date: Feb. 7, 2013

(65) Prior Publication Data
US 2014/0177807 A1    Jun. 26, 2014

Related U.S. Application Data

(60) Provisional application No. 61/515,070, filed on Aug. 4, 2011.

(51) Int. Cl.
*H01J 35/08* (2006.01)
*H01J 1/06* (2006.01)
(Continued)

(52) U.S. Cl.
CPC . *H01J 35/08* (2013.01); *A61B 6/06* (2013.01); *G02B 27/30* (2013.01); *G21K 1/025* (2013.01);
(Continued)

(58) Field of Classification Search
CPC ................ H01J 1/00; H01J 1/02; H01J 1/04; H01J 1/05; H01J 1/06; H01J 1/08; H01J 1/10; H01J 7/00; H01J 7/24; H01J 7/26; H01J 13/00; H01J 13/02; H01J 13/04; H01J 13/16; H01J 13/24; H01J 13/242; H01J 13/244; H01J 13/46; H01J 13/50; H01J 35/00; H01J 35/02; H01J 35/025; H01J 35/04; H01J 35/08; H01J 35/12; H01J 35/16; H01J 35/25; H01J 35/30; H01J 2235/082; H01J 2235/087; H01J 2235/1204; H01J 2235/122; H01J 2235/1262; H01J 2235/1283; H01J 2235/1291; H01J 2235/16; H01J 2235/186; G21K 1/00; G21K 1/02; G21K 1/08; G21K 1/087; G21K 1/093; G21K 1/02508; A61B 6/00; A61B 6/06; A61B 6/40; A61B 6/4035; A61B 6/44; A61B 6/547; H05G 1/00; H05G 1/02; H05G 1/025; H05G 1/08; H05G 1/085; H05G 1/52; H05G 1/56; G02B 27/00; G02B 27/09; G02B 27/027; G02B 27/0938; G02B 27/0988; G02B 27/30
USPC ......... 378/91, 98.5, 98.6, 113, 124, 141, 143, 378/145–149, 165, 193, 199–201; 250/552, 250/553, 206, 555, 557, 215, 396 R, 398, 250/423 R, 424, 427, 428, 432 R, 435–438, 250/493.1, 496.1, 522.1, 526; 359/641
See application file for complete search history.

(56) References Cited

U.S. PATENT DOCUMENTS 3,143,652 A    8/1964  Bigelow
3,509,339 A *  4/1970  Doehner ..................... 250/366
(Continued)

FOREIGN PATENT DOCUMENTS

EP    2711048 A2    3/2014

OTHER PUBLICATIONS

Hatanaka et al., "Photon Energy Conversion of IR Femtosecond Laser Pulses Into X-Ray Pulses Using Electrolyte Aqueous Solutions in Air", American Institute of Physics, 2002; pp. 260-267; extras. springer.com/2002/978-0-7354-0090-4/pdfs/260__1.pdf.
(Continued)

*Primary Examiner* — Anastasia Midkiff
(74) *Attorney, Agent, or Firm* — Dinsmore & Shohl LLP

(57) ABSTRACT

Direct write electron-beam-to-x-ray converters are described, which may be programmed to focus x-rays into an arbitrary shape to provide spatial and intensity modulation to irradiate a malady such as a tumor. An integrated structure of the electron beam to x-ray converter comprises a collimating grid containing a target fluid. The collimating grid comprises a plurality of individual cells enclosed in a housing assembly. An electron beam aimed at a selected individual cell of the collimating grid may be converted to an x-ray beam within the target fluid.

17 Claims, 10 Drawing Sheets

(51) Int. Cl.
|  |  |
|---|---|
| *G21K 1/087* | (2006.01) |
| *G21K 1/093* | (2006.01) |
| *A61B 6/06* | (2006.01) |
| *H05G 1/52* | (2006.01) |
| *G02B 27/30* | (2006.01) |
| *H01J 35/12* | (2006.01) |
| *H01J 35/18* | (2006.01) |
| *H01J 35/30* | (2006.01) |
| *G21K 1/02* | (2006.01) |
| *G21K 1/08* | (2006.01) |
| *A61B 6/00* | (2006.01) |

(52) U.S. Cl.
CPC ............... *G21K 1/087* (2013.01); *G21K 1/093* (2013.01); *H01J 1/06* (2013.01); *H01J 35/12* (2013.01); *H01J 35/18* (2013.01); *H01J 35/30* (2013.01); *H05G 1/52* (2013.01); *A61B 6/40* (2013.01); *A61B 6/4035* (2013.01); *G21K 1/02* (2013.01); *G21K 1/08* (2013.01); *H01J 2235/082* (2013.01); *H01J 2235/087* (2013.01); *H01J 2235/122* (2013.01); *H01J 2235/1204* (2013.01); *H01J 2235/1262* (2013.01); *H01J 2235/1283* (2013.01); *H01J 2235/1291* (2013.01); *H01J 2235/16* (2013.01); *H01J 2235/186* (2013.01)

(56) References Cited

U.S. PATENT DOCUMENTS

| | | | |
|---|---|---|---|
| 4,007,375 | A * | 2/1977 | Albert .......................... 378/113 |
| 4,304,999 | A | 12/1981 | Richey et al. |
| 4,726,046 | A | 2/1988 | Nunan |
| 4,953,191 | A | 8/1990 | Smither et al. |
| 5,665,969 | A | 9/1997 | Beusch |
| 5,799,057 | A | 8/1998 | Hoffman et al. |
| 5,859,893 | A | 1/1999 | Moorman et al. |
| 6,185,277 | B1 * | 2/2001 | Harding ........................ 378/143 |
| 6,744,851 | B2 * | 6/2004 | Orsini et al. .................. 378/119 |
| 6,839,405 | B2 | 1/2005 | Bani-Hashemi et al. |
| 7,141,812 | B2 * | 11/2006 | Appleby et al. ............ 250/505.1 |
| 7,462,852 | B2 * | 12/2008 | Appleby et al. ............ 250/505.1 |
| 7,518,136 | B2 * | 4/2009 | Appleby et al. ............ 250/505.1 |
| 7,589,327 | B2 | 9/2009 | Kerwin |
| 7,785,098 | B1 * | 8/2010 | Appleby et al. ............... 425/470 |
| 8,798,233 | B2 | 8/2014 | Geisler et al. |
| 2002/0048345 | A1 * | 4/2002 | Bachmann et al. ............ 378/121 |
| 2008/0053638 | A1 * | 3/2008 | Appleby et al. ............... 164/129 |
| 2010/0195804 | A1 | 8/2010 | Dafni et al. |
| 2013/0202091 | A1 * | 8/2013 | Haider ......................... 378/145 |

OTHER PUBLICATIONS

International Search Report and Written Opinion completed Sep. 28, 2012 pertaining to International Application No. PCT/US2012/049731.

* cited by examiner

BREMSTRAHLUNG TARGET FOR INTENSITY MODULATED X-RAY RADIATION THERAPY AND STEREOTACTIC X-RAY THERAPY

The present application hereby claims priority under 35 U.S.C. §119(e) to Provisional U.S. Application No. 61/515,070 filed Aug. 4, 2011, entitled "Improved Bremstrahlung Target For Intensity Modulated X-ray radiation Therapy and Stereotatic X-Ray Thereapy."

The present application generally relates to x-ray devices for medical use and more particularly relates to an integrated target and collimating grid for the production of x-rays.

When a high energy electron (~1 to 10 MeV) collides with an atom, some beam energy is lost and the energy loss is converted into gamma-rays (high energy x-rays), inelastic electrons, and heat. Although the conversion from electrons to x-rays is inefficient, there is still a large flux of x-rays. The x-rays can also collide with atoms and emit electrons at energies below the primary. A cascade is generated, often called an electron-gamma shower.

Intensity modulated radiation therapy (IMRT) systems are used to deliver a controlled dose of x-rays to a tumor. To minimize radiation damage to healthy tissue, the patient is irradiated with x-rays from many angles. The IMRT system is mounted on a gantry that rotates around the patient. At a specific gantry position, the x-ray beam is shaped to match the cross section of the tumor at a particular angle. The gantry is moved, a new cross section shape is made and the irradiation continues.

The technology for conventional IMRT targets is high energy electrons are generated in a linear accelerator. The electron beam strikes a heavy metal (usually tungsten) target. Bremstrahlung radiation is produced as x-rays when the electron beam is slowed down in the target. The x-rays are emitted in a large radiation cone. To control the area irradiated, a collimator is installed downstream of the target. The multi-leaf collimator (MLC) is a complex, inter-digitated array of tungsten blocks that are positioned to transmit a part of the x-ray beam to the tumor, but most x-rays are blocked off by the MLC. Drive motors position the blocks to define the aperture shape and how much of the x-rays are blocked out. A significant problem with the MLC's is that the x-rays that are absorbed in the collimator fingers create a secondary radiation shower. This shower irradiates the treatment room and exposes the patient to a low dose of x-rays over the whole body. This whole body exposure has produced some secondary cancers. Additional problems with the MLCs are that the digital fingers stick together and motors overheat due to the large forces needed to position the fingers. In addition the collimators are slow, and expensive.

In addition to the IMRT, there are also commercial radiation therapy systems that use a $^{60}$Co gamma source radiation which is always on, so radiation shielding is very important. In this system over 200 $^{60}$Co sealed sources are installed into a tungsten helmet. The tungsten helmet is designed to only transmit a small fraction of the x-rays out of the helmet. The tungsten shields the environment from lateral x-rays transmission. This technology is usually used to irradiate brain tumors. With the $^{60}$Co system, the helmet collimates the x-rays onto a focal point. The patient's head is secured into the helmet so that the tumor is at the focal point.

Furthermore, in conventional IMRT, the whole region of a tumor is irradiated. There is no spatial separation between different areas or lobes of the tumor.

Therefore there exists a need for a device that can produce complex x-ray beam shapes, can improves safety, and has the ability to be turned off.

The disclosure describes a "direct write," electron-beam-to-x-ray converter that can be programmed to focus x-rays into an arbitrary shape to provide spatial and intensity modulation to irradiate a cancer tumor. An integrated structure comprising a collimating grid and a target fluid is disclosed. The collimating grid comprises a plurality of individual cells, the individual cell being defined by a plurality of cell walls made of an x-ray absorbing material. A housing assembly comprising an upper substrate, a lower substrate, and a frame, wherein the upper substrate and the lower substrate each comprises a foil sheet with a dielectric coating on an interior face of the foil sheet, the upper substrate attaches to an upper edge of the frame, the lower substrate attaches to a lower edge of the frame. The housing assembly encloses the collimating grid and is fillable with the target fluid.

Another object of the disclosure is a direct write electron to x-ray converter apparatus comprising the integrated structure, a pair of steering magnets, an electron linear accelerator, and an ionization chamber. The electron linear accelerator is configured to produce an electron beam and aim the electron beam between the pair of steering magnets. The pair of steering magnets are configured to raster an electron beam into one or more individual cells, the individual cell is configured to produce an x-ray beam when struck by the electron beam.

Another object of the disclosure is the method of producing an x-ray beam, the method comprising: projecting an electron beam created by the linear accelerator onto the integrated structure; introducing a target fluid into the integrated structure; and steering the electron beam with a pair of steering coils into the individual cell configured to produce an x-ray beam when struck by the electron beam.

The present disclosure will become more fully understood from the following detailed description, taken in conjunction with the accompanying figures, wherein like reference numerals refer to like elements, in which.

Figure 6:
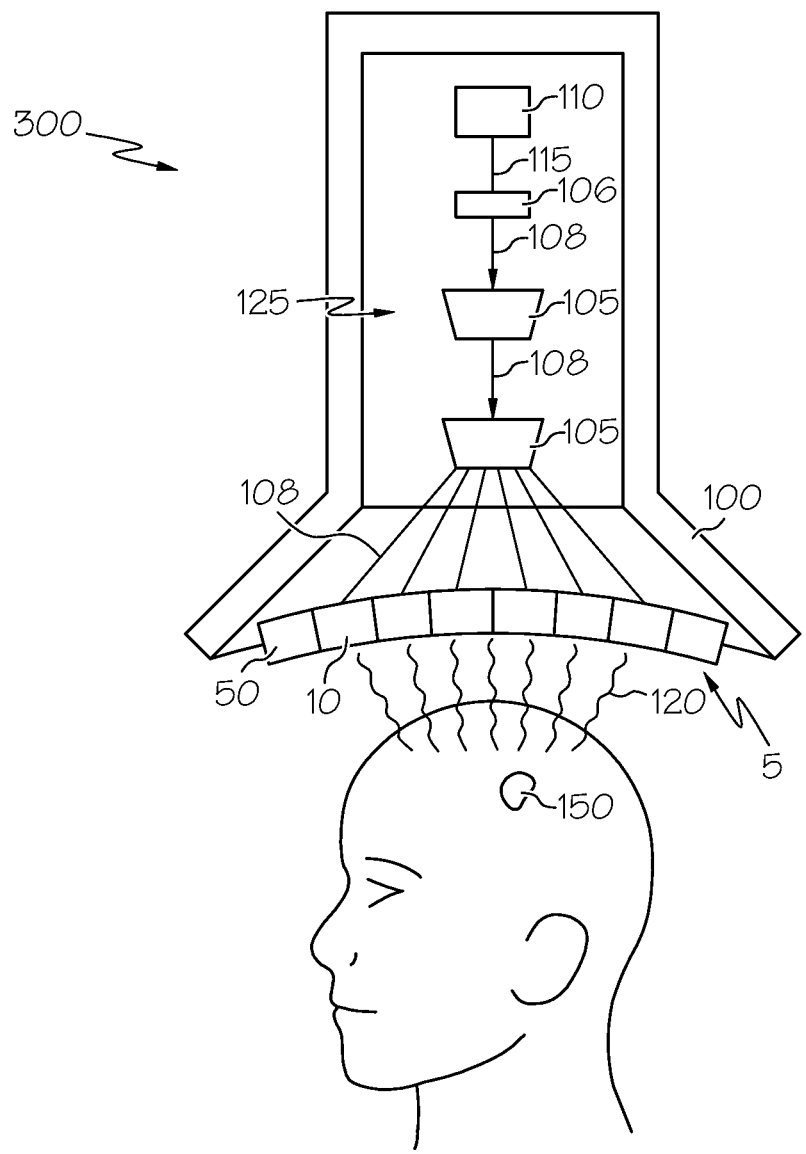
Figure 7:
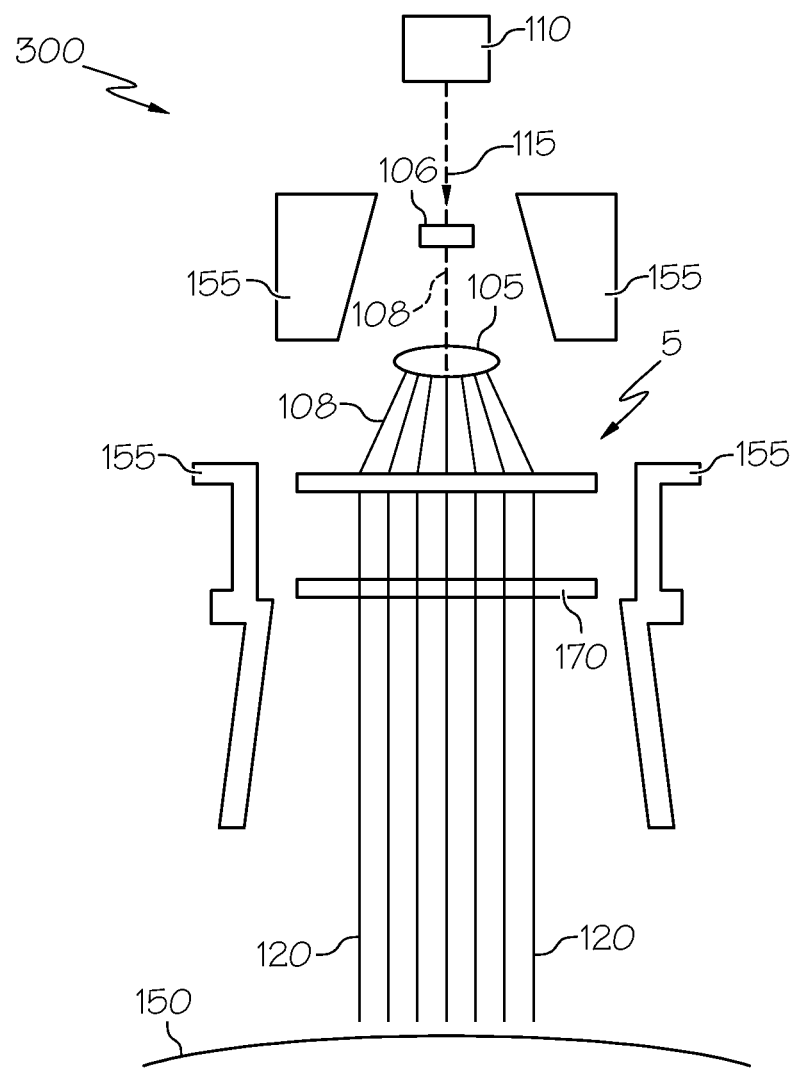
Figure 8A:
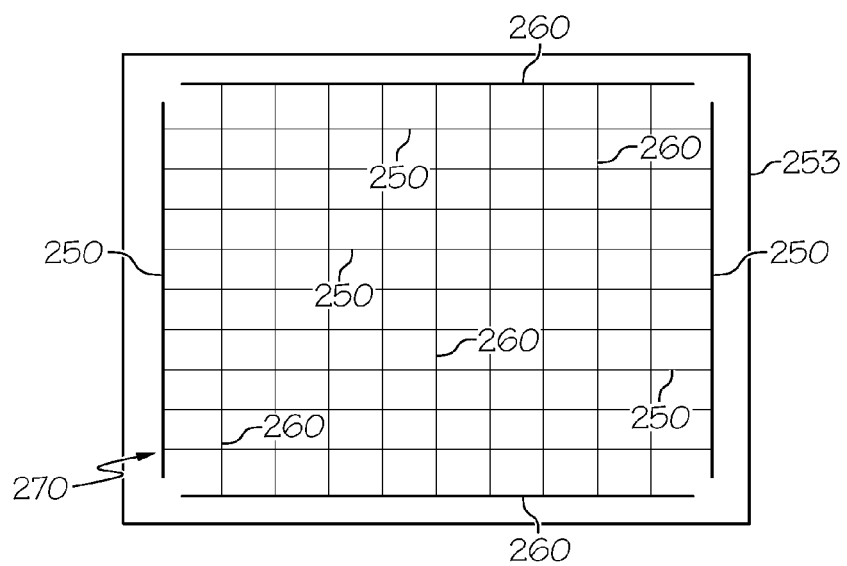
Figure 8B:
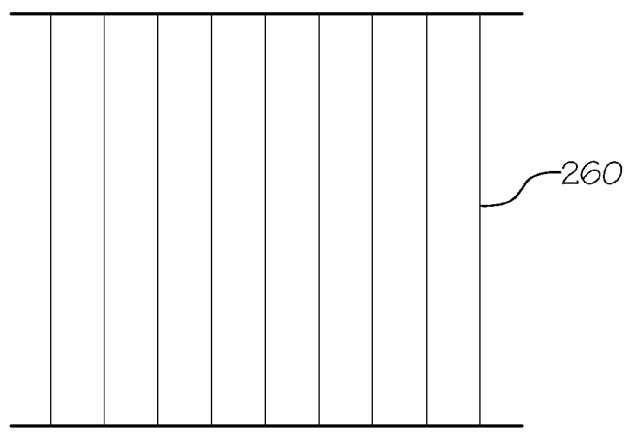
Figure 8C:
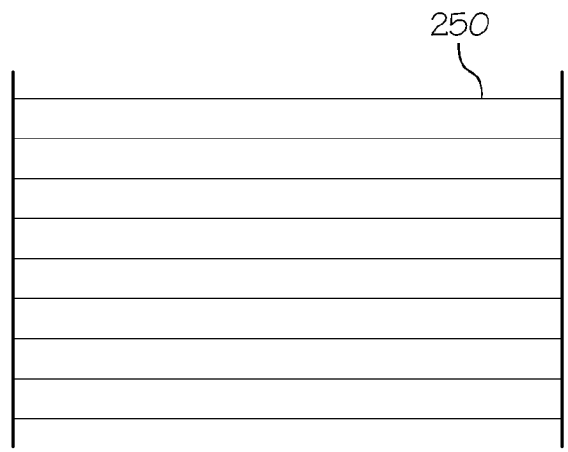
Figure 9:
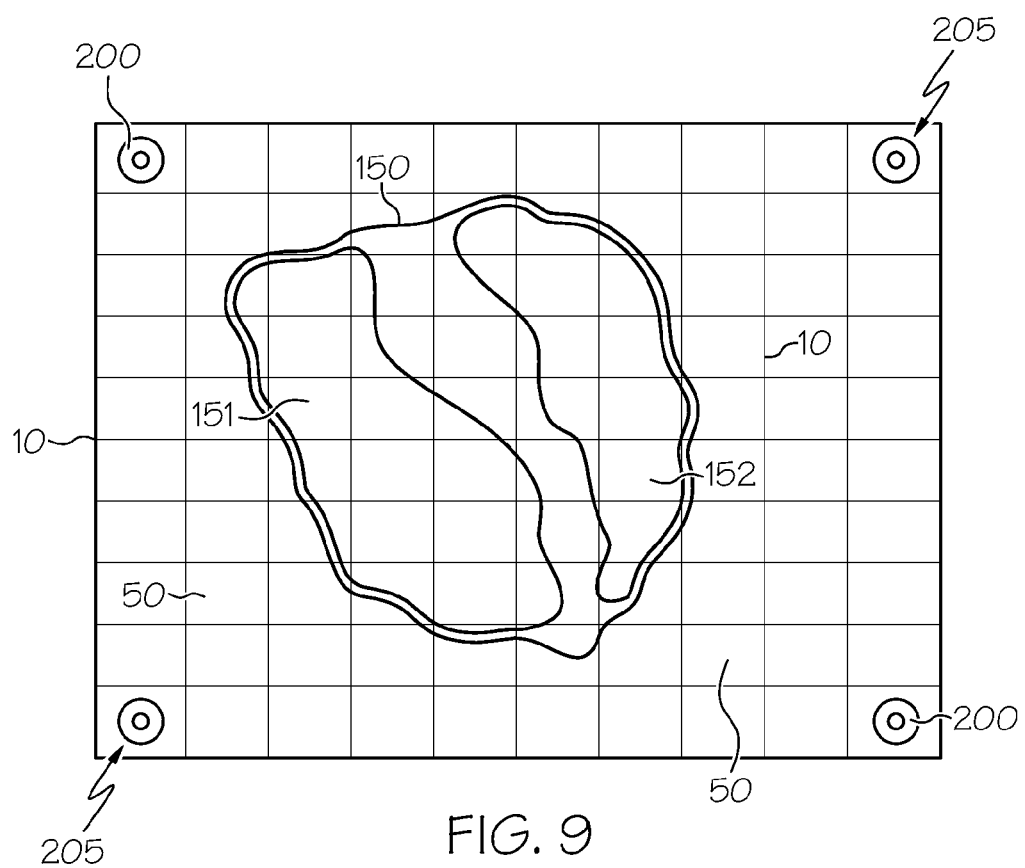

FIG. 6. is a perspective view of the Bremstrahlung target apparatus in an arc-type configuration;

FIG. 7 is a side view of the Bremstrahlung target apparatus;

FIGS. 8A, 8B, and 8C depict a top view of a ionization chamber and a plurality of anode wires and a plurality of cathode wires;

FIG. 9 is a top view of the integrated structure over a tumor; and

Figure 10:
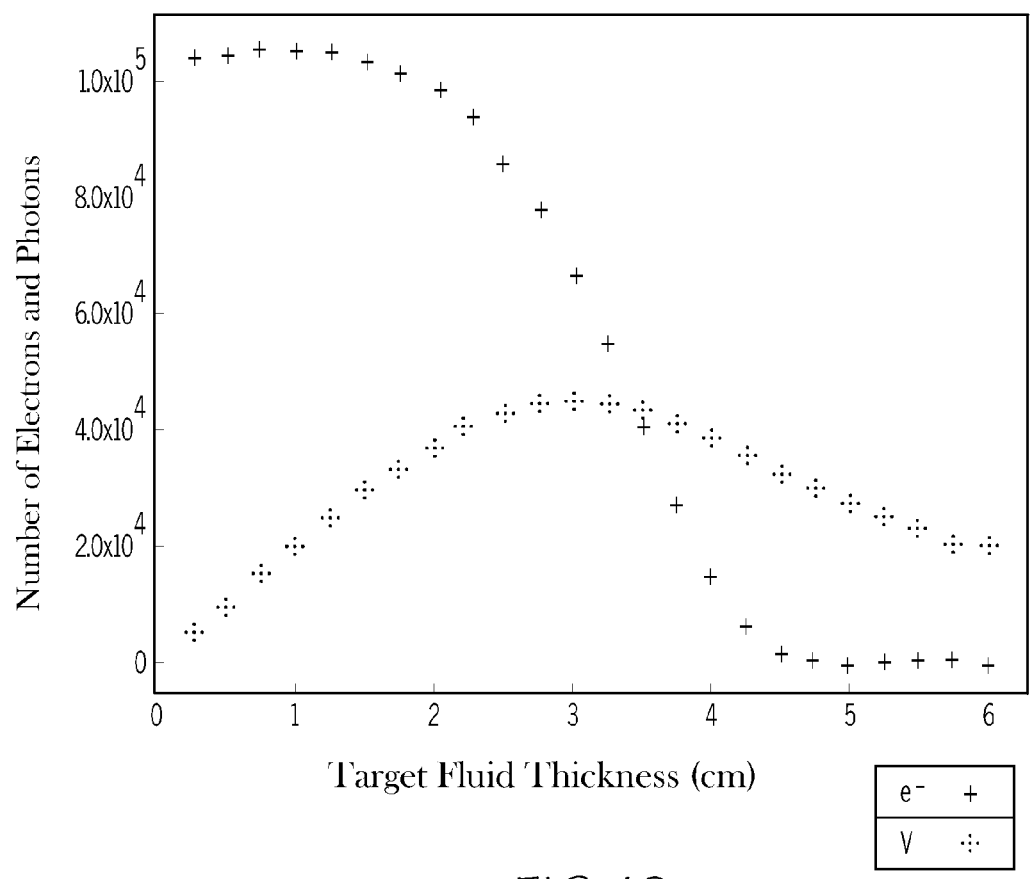

FIG. 10 plots the intensity of electrons in the Bremstrahlung target apparatus.

Before turning to the figures, which illustrate several embodiments in detail, it should be understood that the application is not limited to the details or methodology set forth in the description or illustrated in the figures. It should also be understood that the terminology is for the purpose of description only and should not be regarded as limiting. For example, terms such as "left," "right," "front," "back," "upper," and "lower" are used herein as a matter of convenience, particularly with reference to the drawings. These terms are not intended to be limiting to a particular orientation, nor are they intended to indicate a preferred orientation, except where noted otherwise.

The present application discloses a spatially and intensity modulated radiation therapy (IMRT) collimator with an integrated target. The spatially IMRT collimator with an integrated target is a direct write apparatus that uses an electron beam to serve two functions. First, the electron beam may be used to produce an x-ray beam. Second, the electron beam may also be used to indicate a direction of travel for the x-ray beam to hit an object. In some embodiments, the object may be a tumor that is the subject of the IMRT treatment.

Figure 1:
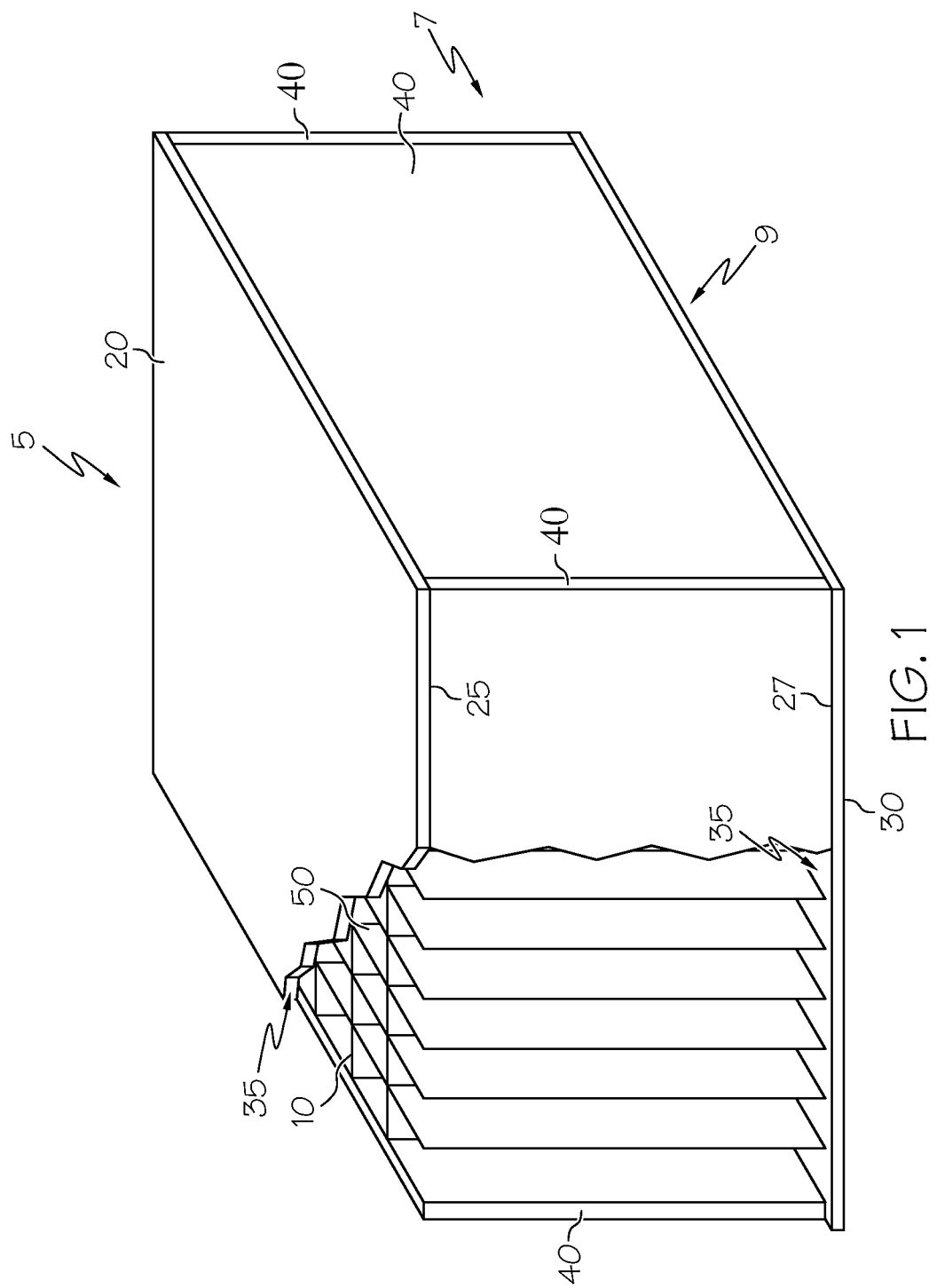
FIG. 1 is a perspective view of an integrated structure in a housing assembly.
Figure 2:
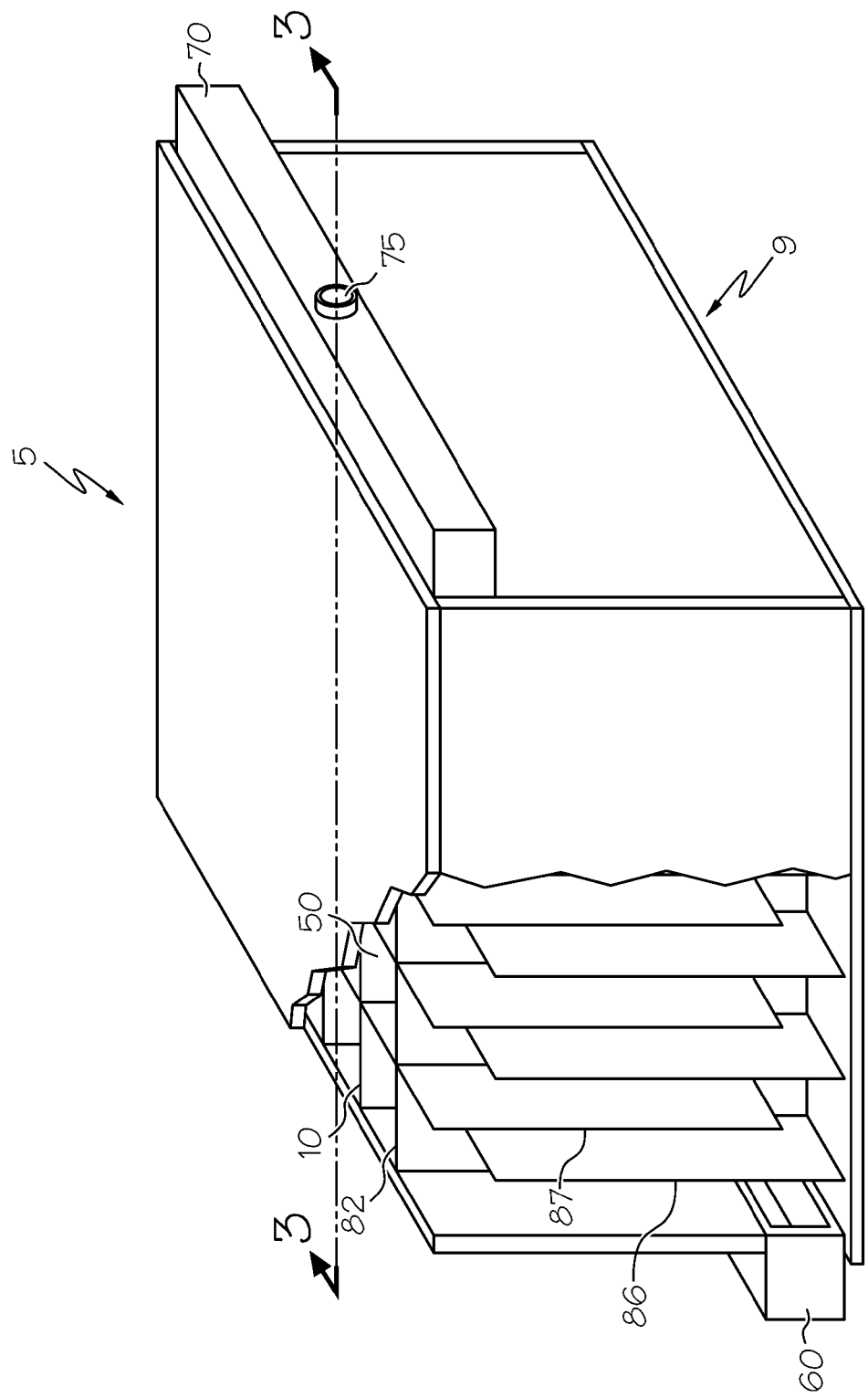
FIG. 2 is a perspective view of the integrated structure in the housing assembly configured to allow fluid flow through the housing assembly.

A core structure of the direct write apparatus is an integrated structure 5. FIG. 1 depicts the integrated structure 5 comprising a collimating grid 10 enclosed in a housing assembly 9. In some embodiments, the housing assembly 9 may contain or be filled with a target fluid. In other embodiments, the housing assembly 9 may contain the target fluid, and the target fluid may be circulated through the housing assembly 9. The collimating grid 10 is a device used to allow a parallel beam of radiation to pass through unimpeded while stopping the passage of scattered radiation from exiting the collimating grid 10. This allows the integrated structure 5 to hit an object such as a tumor 150, as shown in FIG. 9, with radiation without exposure to a peripheral field of the tumor 150. The collimating grid 10 may comprise a plurality of individual cells 50. The individual cells 50 are tessellated to form the collimating grid 10. In one non-limiting illustrative embodiment, the collimating grid 10 is configured as a grid of squares or rectangles, as shown in FIGS. 1 and 2. It should be understood that other geometric configurations are possible, such as a grid of hexagons, or a grid of other shapes that may be tessellated in a space-filling manner. The individual cell 50 may be defined by a plurality of cell walls made of an x-ray absorbing material. In some embodiments, the x-ray absorbing material may be a heavy metal such as tungsten, tantalum, or lead, for example.

The housing assembly 9 comprises an upper substrate 20, a lower substrate 30, and a frame 7. The frame 7 provides structural support for the integrated structure 5. The frame 7 comprises a plurality of individual walls 40. Each individual wall 40 has an upper edge 25, and a lower edge 27. The plurality of individual walls 40 are arranged to surround the collimating grid 10 and form the frame 7. The frame 7 is not limited to only four individual walls 40 but can be of any amount needed to fulfill the needs of the integrated structure 5. The upper substrate 20 is attached the upper edge 25 of the frame 7 and the lower substrate 30 attaches to the lower edge 27 of the frame 7 to enclose the collimating grid 10 such that the target fluid may be retained in the plurality of individual cells 50.

Both the upper substrate 20 and the lower substrate 30 may be constructed from a thin, low density sheet metal to minimize the production of an x-ray. In some embodiments, the upper substrate 20 and the lower substrate 30 may be made from aluminum, beryllium, stainless steel, or sheet metal, and are as thin as possible to minimize the production of the x-ray, e.g. 0.127 mm (0.005 inches) for beryllium. In some embodiments, the upper substrate 20 and the lower substrate 30 are a foil sheet with a dielectric coating on an interior face 35 of the foil sheet can be used for both the upper substrate 20 and the lower substrate 30.

During operation of a direct write apparatus including the integrated structure 5, individual cells 50 of the collimating grid 10 may be filled with the target fluid. The target fluid may be a low density material that is capable of producing an x-ray shower when bombarded with electrons. The x-ray shower is described in greater detail below. In some embodiments the target fluid is a dielectric liquid, such as distilled water or alcohol.

Figure 3:
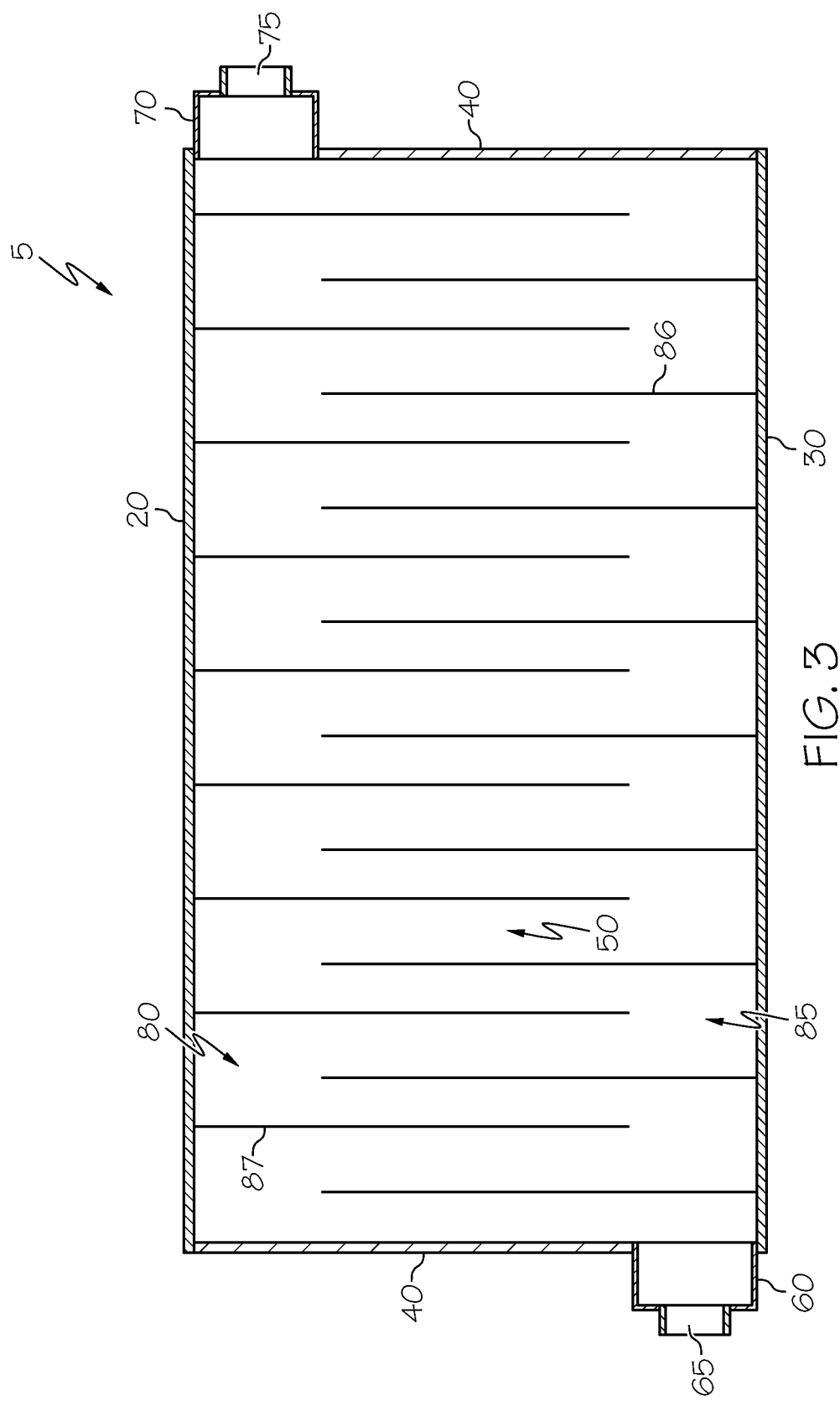
FIG. 3 is a cross-section of the integrated structure in the housing assembly configured to allow fluid flow through the housing assembly.

Referring to FIGS. 2 and 3, the target fluid may be circulated through the integrated structure 5 to cool the collimating grid 10. In an exemplary configuration shown in FIG. 3, an inlet 75 and an outlet 65 may be attached to opposite ends of the housing assembly. In such a configuration, the inlet 75 may be attached to an inlet manifold 70, and the outlet 65 may be attached to an outlet manifold 60. In the embodiments of FIGS. 2 and 3, the collimating grid 10 is a series of alternating vertical walls 86, 87 and vertical walls 82 that create the plurality of cell walls of the individual cells 50. The vertical walls 86, 87 are a series of alternating upper vertical walls 87 and lower vertical walls 86 that define a plurality of upper cavities 80 and a plurality of lower cavities 85. As the target fluid is circulated through the housing assembly from the inlet 75 to the outlet 65, the target fluid flows in a serpentine fluid flow path from the inlet 75 to the outlet 65, through the plurality of upper cavities 80 and the plurality of lower cavities 85 as it passes over the lower vertical walls 86 and under the upper vertical walls 87. The serpentine fluid flow path allows for the individual cell 50 to remain filled with the target fluid and also enables maximum surface contact with the plurality of cell walls to cool the collimating grid 10.

In some embodiments, the collimating grid may comprise vertical walls 82 that define rows of individual cells 50. Alternating upper vertical walls 87 and lower vertical walls 86 define the serpentine flow paths through the individual cells 50 in each row of individual cells. The housing assembly 9 further comprises the inlet 75 in fluidic communication with the serpentine flow paths and the outlet 65 in fluidic communication with the serpentine flow paths. Circulating the target fluid through the serpentine flow paths while the electron beam is projected onto the integrated structure 5 allows target fluid at a hotter temperature from the interaction with the electron beam within the individual cells 50, to be circulated out of the integrated structure 5 and cooled before being re-circulated back into the integrated structure 5.

FIG. 3 depicts a cross-section of the embodiment of FIG. 2. The frame 7 and the upper substrate 20 and the lower substrate 30 enclose the collimating grid 10 and contain the target fluid. FIG. 3 illustrates the upper vertical wall 87 and the lower vertical wall 86 and the serpentine-like fluid flow path from the inlet 75 to the outlet 65, through which the target fluid may be circulated such that the target fluid traverses through the plurality of upper cavities 80 and the plurality of lower cavities 85. Thus, the inlet 75 and inlet manifold 70 are in fluidic communication with the serpentine-like fluid flow path, the outlet manifold 60, and the outlet 65.

Figure 4:
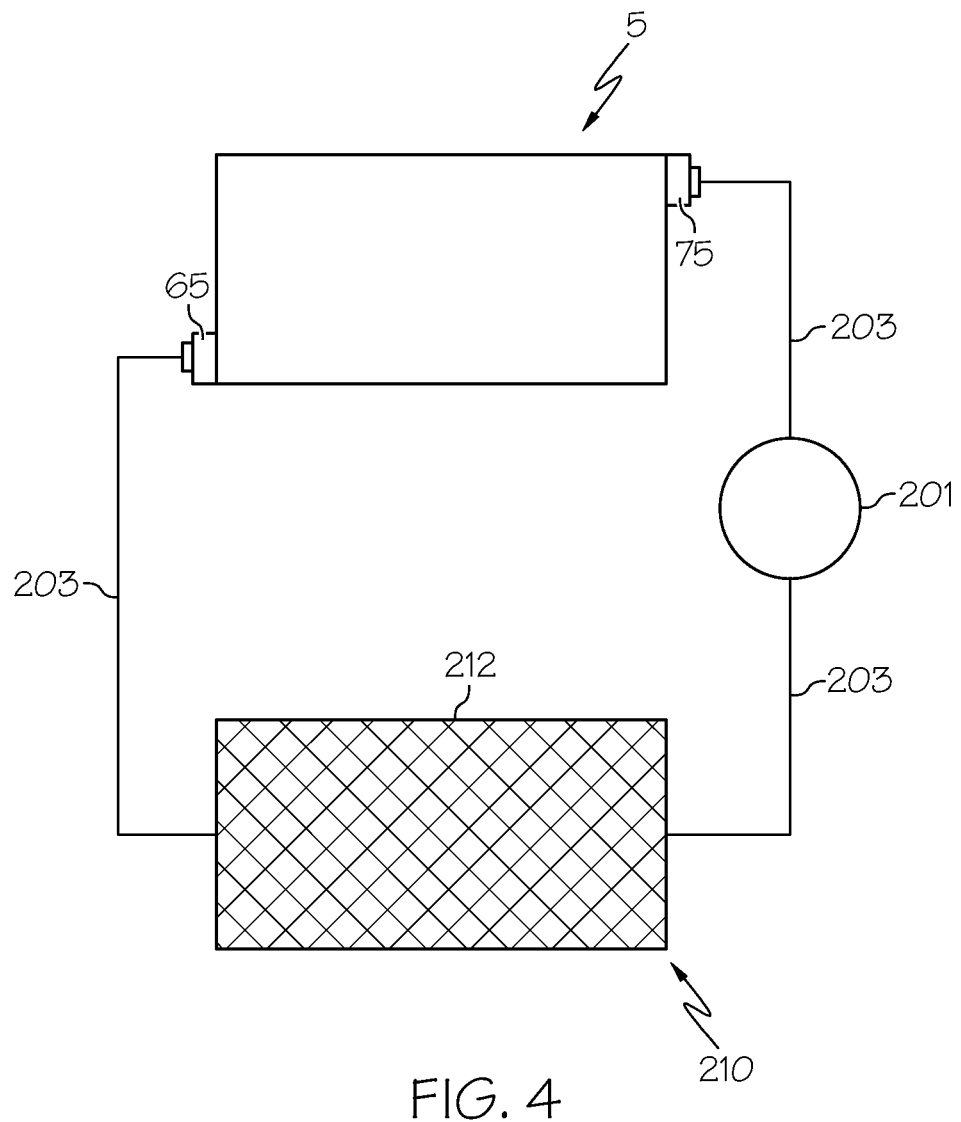
FIG. 4 is a schematic view of the cooling system for the integrated structure.

FIG. 4 is a schematic view of an embodiment of a cooling system for the integrated structure 5. A heat exchanger 210 cools the target fluid by transferring the heat from the target fluid through a body 212 of the heat exchanger 210 to the atmosphere. An airflow through the heat exchanger 210 may be provided by a fan or such mechanism to increase a speed of heat transfer from the target fluid to the atmosphere. A pump 201 circulates the target fluid through the inlet 75 of the integrated structure 5, the outlet 65 and to the heat exchanger 210. A piping network 203 fluidly connects the pump 201, heat exchanger 210, and the integrated structure 5.

Figure 5:
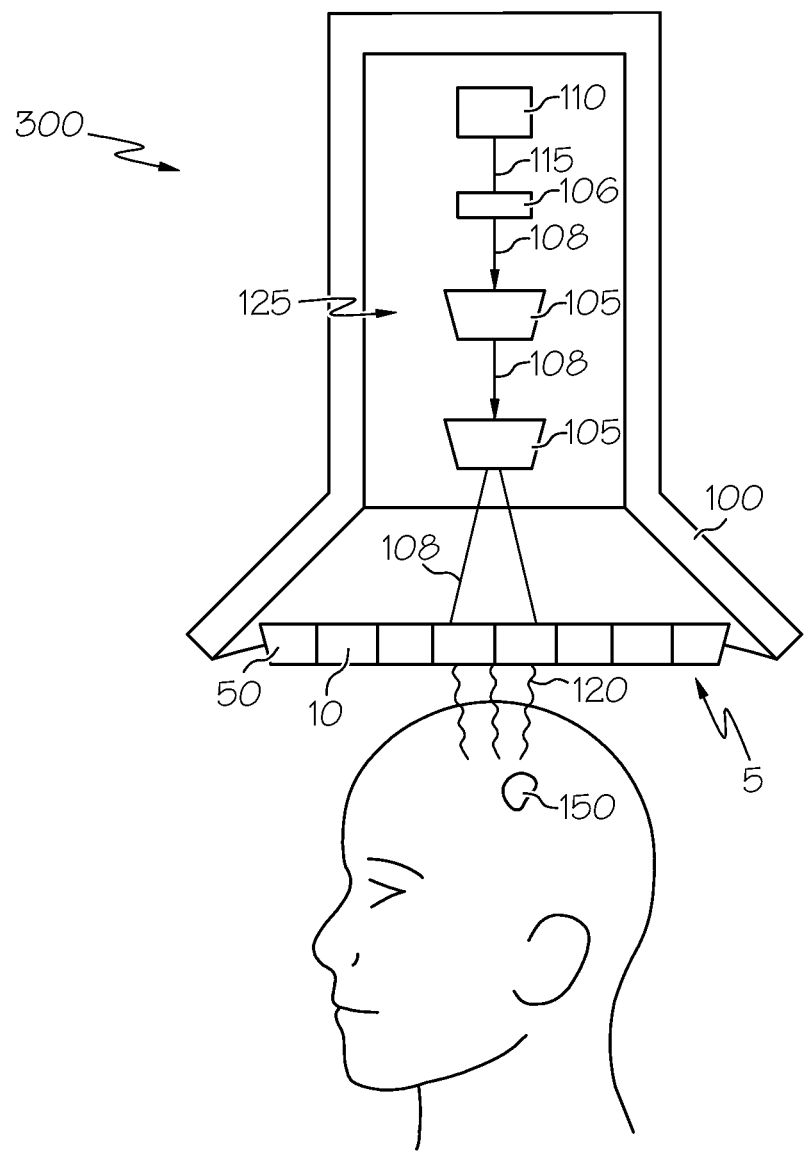
FIG. 5 is a perspective view of an Bremstrahlung target apparatus in a planar-type configuration.

FIG. 5 depicts an embodiment the direct write apparatus 300 in a planar-type configuration. A vacuum housing 100 encloses a linear accelerator 110, a focusing magnet 106, a pair of steering coils 105 and the integrated structure 5 in a vacuum space 125. The linear accelerator 110 produces a stream of high energy electrons or an electron beam 115. The electron beam 115 is focused into a pencil beam 108 by the focusing magnet 106. The pencil beam 108 is directed at the plurality of individual cells 50 through the pair of steering coils 105. The pair of steering coils 105 each uses a magnetic field to raster the pencil beam 108 across the integrated structure 5. As each individual cell 50 is struck with an electron from the pencil beam 108, the individual cell 50 produces x-ray radiation or an x-ray beam 120. The collimating grid 10 absorbs scattered x-rays and produces the x-ray beam 120 in a direction that is parallel to the cell wall of the individual cell 50. The x-ray beam 120 is focused on a tumor 150 by the selection of which individual cells 50 to raster with the electron beam 115. In the planar configuration, the x-ray beam 120 from the individual cells 50 are emitted parallel to x-ray beams 120 from other individual cells 50. The focusing magnet 106 may be a quadrupole magnet.

FIG. 6 depicts an embodiment of the direct write apparatus 300 in an arc configuration. The vacuum housing 100 encloses the linear accelerator 110, the focusing magnet 106, the pair of steering coils 105 and the integrated structure 5 in the vacuum space 125. The linear accelerator 110 produces the electron beam 115 and aims the electron beam at the integrated structure 5. The electron beam 115 is focused into a pencil beam 108 with the focusing magnet 106. The pencil beam 108 is directed at the plurality individual cells 50 through the pair of steering coils 105. The pair of steering coils 105 each uses a magnetic field to raster the pencil beam 108 across the integrated structure 5. As each individual cell 50 is struck with an electron from the pencil beam 108, the individual cell 50 produces an x-ray beam 120. The collimating grid 10 absorbs scattered x-rays and produces a parallel x-ray beam 120. The x-ray beam 120 is focused on a tumor 150 by the selection of which individual cells 50 to raster with the electron beam 115 in combination with a curvature of the arc of the integrated structure 5. The arc embodiment may be configured to produce a concentrated x-ray beam 120 that is focused on the tumor 150.

FIG. 7 is a side view of the direct write apparatus 300. A set of shields 155 protect the environment from scattered electrons and x-rays. The linear accelerator 110 produces the electron beam 115. The electron beam 115 is focused into a pencil beam 108 with the focusing magnet 106. In one embodiment, the pencil beam 108 may be focused to a spot that is smaller than the width of the individual cell 50 (see FIG. 9). In another embodiment, the pencil beam 108 may be focused to a spot that is smaller than the width of the individual cell 50 but is also greater than 50% of the width of the individual cell 50. Generally, the pencil beam 108 need not be focused to less than 50% of the width of the individual cell 50, because the beam scatters within the individual cell 50. In one embodiment, a wall thickness of the cell wall of the individual cell 50 may be about 20% of the width of the individual cell 50. The pencil beam 108 may be directed at the individual cell 50 using the pair of steering coils 105. The pair of steering coils each uses a magnetic field to raster the electron beam 115 across the integrated structure 5. As each individual cell 50 is struck with the electrons from the pencil beam 108, the individual cell produces the x-ray beam 120. An ionization chamber 170 is placed in the x-ray beam 120 path and used to provide additional information on where the x-ray beam is being produced in the integrated structure 5.

FIG. 8A depicts a top view of the ionization chamber 170. The ionization chamber 170 comprises a plurality of individual anode wires 250 and a plurality of individual cathode wires 260 in an enclosure 253. The enclosure may be made from a low-density material. In some embodiments, the enclosure may be made from the same material as the upper substrate and the lower substrate. The plurality of individual anode wires 250 and the plurality of individual cathode wires 260 are electrically isolated from each other and configured to form an ionization grid 270. The ionization grid 270 is configured to match the size, shape, and orientation of the collimating grid 10. The ionization grid 270 is filled with a noble gas such as, for example, argon. The ionization chamber 170 confirms the position of the x-ray beam 120 by detecting a current flow as the noble gas ionizes between an individual anode wire 250 and an individual cathode wire 260 when the x-ray beam 120 passes through the ionization grid 270. X-ray flux in the individual cell 50 of the collimating grid 10 may be detected in the ionization chamber 170 as the noble gas ionizes between the individual anode wire 250 and the individual cathode wire 260 when the x-ray beam 120 passes through the ionization grid 270.

FIG. 8B depicts the plurality of cathode wires 260 of the ionization grid 270 and FIG. 8C depicts the plurality of anode wires 250 of the ionization grid 270. The plurality of cathode wires 260 and the plurality of anode wires 250 may be connected to a computer (not shown). The computer may be used to detect the ionization of the noble gas between the plurality of cathode wires 260 and the plurality of the anode wires 250 and track where the x-ray beam 120 is passing through the ionization grid 270. The computer may compare the detection of the x-ray beam in the ionization grid to a detected position from the collimating grid as described below.

FIG. 9 depicts the collimating grid 10 over the tumor 150. The computer may be used to take a real time image of the tumor 150 and move the direct write apparatus 300 into position to bombard the tumor 150 with x-rays. The direct write apparatus 300 is attached to a gantry that allows the computer to move the direct write apparatus 300 into an irradiation position. The collimating grid 10 comprises a plurality of individual calibration points 200 positioned at a plurality of individual outer positions 205 in the collimating grid 10. The computer comprises a processor which is electrically connected to the pair of steering coils 105 and the plurality of individual calibration points 200. The processor directs the pair of steering coils 105 to aim the electron beam 115 at an individual calibration point 200 and the individual calibration point 200 indicates to the processor when the individual calibration point 200 is struck by the electron beam 115. This enables the processor to know where the steering coils 105 are directing the electron beam 115 and to determine if the electron beam 115 is not striking the correct individual cell 50. If the electron beam 115 is not striking the correct individual cell 50, the processor can calibrate the pair of steering coils so the electron beam 115 strikes the individual cell 50 desired. In one embodiment, the individual calibration points 200 may be sensors such as small Faraday cups, and the pair of steering coils 105 may be calibrated at the beginning of treatment.

In some embodiments, the collimating grid 10 may be electrically isolated from the housing assembly. This may enable a collimating current to be detected. The collimating current may be used to determine which individual cells 50 are producing the x-ray beam at any given time. The collimating grid 10 is electrically connected to a position detection device. The position detection device is configured to indicate the detected position of the x-ray beam or which individual cell 50 is being struck by the electron beam. The computer may then compare the detected position to the detection of the x-ray beam in the ionization grid to confirm where the x-ray beam is being produced and projected.

The electron beam 115 may be focused onto the individual cell 50 and maintained in a fixed position until a specified x-ray dose is delivered to the tumor 150. Because healthy, non-tumor cells are at risk for receiving exposure to the x-ray beam 120, a treatment plan would decide how to irradiate a partial overlap where the tumor 150 is only partially covered by the individual cell 50. One possible solution is to move the direct write apparatus 300 so that the part of the tumor 150 that was not irradiated is fully covered by the individual cell 50 and healthy cells would no longer be at risk of exposure to the x-ray beam 120. The duration of exposure to the x-ray beam 120 would depend on a density of the tumor 150. The precision of the integrated structure 5 may be determined by a ratio of an individual cell 50 cross-sectional area when looking from the top view as in FIG. 9, to the thickness of the collimating grid 10 as viewed from the cross sectional view in FIG. 3. Furthermore, the individual cell cross-sectional area determines the size of the x-ray beam 120 transmitted through the collimating grid 10. An individual cell wall thickness controls how well the x-rays in one individual cell 50 scatter into an adjacent individual cell 50. The plurality of cell walls of a selected individual cell 50 shield individual cells 50 adjacent to the selected individual cell from the x-ray shower and, therefore, collimate the x-ray shower in the selected individual cell 50 into which the electron beam 115 is being focused.

Furthermore, because the electron beam 115 may be directed to a specific individual cell 50, the electron beam 115 can treat more than one area of the object such as the tumor 150. For example, as shown in FIG. 9, the tumor 150 may have multiple lobes such as a first lobe 151 and a second lobe 152. By limiting the production of an x-ray beam to only selected individual cells 50 above exactly one of the individual lobes, the x-ray beam 120 may be directed to treat each lobe separately. The electron beam 115 and the resulting x-ray beam 120 may also be directed at multiple tumors or targets instead of multiple lobes of the tumor 150.

A complex x-ray beam shape may be produced by the combination of modulating an intensity of the x-ray beam 120 and rastering the electron beam 115 across at least one or more individual cells 50. Modulation or adjustment of a current source electrically connected to the linear accelerator 110 varies the amount of electrons being produced and modulates the electron beam 115. As the electron beam 115 is modulated, the amount of x-rays being produced in the individual cells 50 is also being varied and modulates the intensity of the x-ray beam 120. The intensity of the x-ray beam 120 affects the dosing amount the tumor 150 will receive. The complex x-ray beam shape allows precision for the direct write apparatus 300 to only dose tumorous cells of the tumor 150 and not dose neighboring healthy cells.

FIG. 10 plots a thickness of the target fluid versus the number of electrons remaining from the electron beam as the electrons are absorbed by the target fluid when the target fluid is bombarded with the electron beam. In FIG. 10, the number of electrons remaining and the number of x-rays that are produced by the electrons interacting with the target fluid are represented by the "+" symbol. The number of photons are represented by the diamonds. The x-axis is the thickness of the target fluid in centimeters. The thickness of the target fluid exhibits a one-to-one relationship with the thickness of the collimator as described above. The y-axis is the number of the electrons and x-rays (photons).

The target fluid is chosen and configured to convert as many electrons from the electron beam as possible to x-rays in the x-ray beam and to maximize the number of x-rays in the x-ray beam that are delivered for treatment of the tumor. For example, the electron beam delivering 6 MeV and striking the target fluid would optimize x-ray production with a target fluid thickness of at least 4 cm as shown in FIG. 10. In addition FIG. 10 illustrates that the 6 MeV electron beam is fully absorbed by the 4 cm target fluid. Therefore, the x-ray production reaches a maximum intensity. The target fluid thickness is measured as the height of the target fluid as it fills the individual cell 50 in FIG. 3. The target fluid may be thinner for lower energy electron beams and thicker for higher energy electron beams.

The dielectric coatings on the upper substrate 20 and the lower substrate 30 electrically isolate the collimating grid 10 from the housing assembly 9. As the electron beam strikes the collimating grid 10, an electron beam 115 position can be tracked by measuring an electric current within the collimating grid 10. By electrically isolating the collimating grid 10 from the housing assembly 9, the x-y position of the electron beam 115 can be measured. This ensures that the electron beam 115 is striking the correct individual cell 50.

The direct write apparatus 300 may use the computer to control and monitor various aspects the integrated structure 5, the ionization chamber 170, the gantry, and in the formation of the complex x-ray beam shape. For example, the computer may be used to track the position of the electron beam 115 using the collimating current within the collimating grid 10 and reporting that position via a display. The computer may also be used to track the position of the x-ray beam 120 as it passed through the ionization chamber 170. The current flow as the x-ray beam passes through the noble gas is detected and reported by the computer to a display. Furthermore, the computer may be used to control the gantry to move the direct write apparatus 300 into position to irradiate the tumor 150. Finally the computer may be used to adjust or modulate the current source of the linear accelerator 110 and the pair of steering coils 105 to create the proper complex x-ray beam shape to irradiate the tumor 150.

While the present disclosure has been particularly shown and described with reference to specific embodiments, it should be understood by those skilled in the art that various changes in form and detail may be made therein without departing from the spirit and scope of the disclosure as defined by the appended claims.

The invention claimed is:

1. An integrated structure comprising:
   a collimating grid comprising a plurality of individual cells, each individual cell being defined by a plurality of cell walls made of an x-ray absorbing material;
   a housing assembly enclosing the collimating grid, the housing assembly comprising an upper substrate, a lower substrate, and a frame, wherein the upper substrate and the lower substrate each comprises a foil sheet with a dielectric coating on an interior face of the foil sheet, the upper substrate attaches to an upper edge of the frame, and the lower substrate attaches to a lower edge of the frame,
   wherein the housing assembly is configured to hold a target fluid that at least partially fills the individual cells, whereby x-ray radiation is produced when an electron beam is directed through a selected individual cell containing the target fluid.

2. The apparatus of claim 1, wherein the foil sheet of the upper substrate and the lower substrate are made from aluminum, stainless steel, or beryllium.

3. The apparatus of claim 1, wherein the x-ray absorbing material is tungsten, tantalum, or lead.

4. The apparatus of claim 1, wherein:
the collimating grid comprises:
vertical walls that define rows of individual cells; and
alternating upper vertical walls and lower vertical walls that define serpentine flow paths through the individual cells in each row of individual cells; and
the housing assembly further comprises an inlet in fluidic communication with the serpentine flow paths and an outlet.

5. A direct write electron to x-ray converter apparatus comprising:
an integrated structure comprising:
a collimating grid comprising a plurality of individual cells, each individual cell being defined by a plurality of cell walls made of an x-ray absorbing material;
a housing assembly enclosing the collimating grid, the housing assembly comprising an upper substrate, a lower substrate, and a frame, wherein the upper substrate and the lower substrate each comprises a foil sheet with a dielectric coating on an interior face of the foil sheet, the upper substrate attaches to an upper edge of the frame and, the lower substrate attaches to a lower edge of the frame; and
a target fluid contained within the housing assembly and at least partially filling the individual cells;
an electron linear accelerator that produces an electron beam, the electron linear accelerator being configured to aim the electron beam toward the integrated structure; and
a pair of steering magnets configured to raster the electron beam toward one or more selected individual cells of the integrated structure, whereby an x-ray beam is formed in the target fluid when the electron beam passes through the one or more selected individual cells.

6. The apparatus of claim 5, wherein the integrated structure is a curved integrated structure that focuses the x-ray beam to a focal point.

7. The apparatus of claim 5, further comprising a plurality of individual calibration points positioned at a plurality of individual outer positions of the collimating grid.

8. The apparatus of claim 5, wherein:
the collimating grid is electrically isolated from the housing assembly; and
the apparatus further comprises a position detection device electrically connected to the collimating grid and configured to detect which individual cell is being struck by the electron beam.

9. The apparatus of claim 5, further comprising an ionization chamber containing a noble gas, the ionization chamber comprising an ionization grid configured to match the size, shape, and orientation of the collimating grid, the ionization grid comprising a plurality of individual anode wires and a plurality of individual cathode wires electrically isolated from the plurality of individual anode wires.

10. The apparatus of claim 9, wherein the noble gas is argon.

11. The apparatus of claim 5, wherein the foil sheet is made of aluminum, stainless steel, or beryllium.

12. The apparatus of claim 5, wherein the target fluid is distilled water or alcohol.

13. The apparatus of claim 5, wherein the x-ray absorbing material is tungsten, tantalum, or lead.

14. A method of producing an x-ray beam, the method comprising:
projecting an electron beam onto an integrated structure of a direct write electron to x-ray converter apparatus, the direct write electron to x-ray converter apparatus comprising:
the integrated structure comprising:
a collimating grid comprising a plurality of individual cells, the individual cell being defined by a plurality of cell walls made of an x-ray absorbing material;
a housing assembly enclosing the collimating grid, the housing assembly comprising an upper substrate, a lower substrate, and a frame, wherein the upper substrate and the lower substrate each comprises a foil sheet with a dielectric coating on an interior face of the foil sheet, the upper substrate attaches to an upper edge of the frame and, the lower substrate attaches to a lower edge of the frame; and
a target fluid contained within the housing assembly and at least partially filling the individual cells;
an electron linear accelerator that produces the electron beam and aims the electron beam toward the integrated structure; and
a pair of steering magnets configured to raster the electron beam toward one or more individual cells; and
steering the electron beam into a selected individual cell to produce the x-ray beam in the target fluid contained within the one or more selected individual cell.

15. The method of claim 14, further comprising
rastering the electron beam across the plurality of individual cells.

16. The method of claim 14, wherein the direct write electron to x-ray converter apparatus further comprises an ionization chamber containing a noble gas, the ionization chamber comprising an ionization grid configured to match the size, shape, and orientation of the collimating grid, the ionization grid comprising a plurality of individual anode wires and a plurality of individual cathode wires electrically isolated from the plurality of individual anode wires, the integrated structure being disposed between the electron linear accelerator and the ionization chamber, the method further comprising:
detecting a current flow in the ionization grid to determine an ionization-grid position of the x-ray beam;
detecting a position of the x-ray beam in the collimating grid; and
comparing the ionization-grid position of the x-ray beam to the position of the x-ray beam detected in the collimating grid to determine whether the one or more selected individual cells of the integrated structure are producing the x-ray beam.

17. The method of claim 14, wherein:
the collimating grid comprises:
vertical walls that define rows of individual cells; and
alternating upper vertical walls and lower vertical walls that define serpentine flow paths through the individual cells in each row of individual cells; and
the housing assembly further comprises an inlet in fluidic communication with the serpentine flow paths and an outlet,
the method further comprising:
circulating the target fluid through the serpentine flow paths while the electron beam is projected onto the integrated structure.

* * * * *